United States Patent [19]
Campbell

[11] Patent Number: 5,461,436
[45] Date of Patent: Oct. 24, 1995

[54] COLOR FIELD TEST WITH OCCLUSION OF NON-TESTED EYE

[75] Inventor: Charles E. Campbell, Berkeley, Calif.

[73] Assignee: Humphrey Instruments, Inc., San Leandro, Calif.

[21] Appl. No.: 145,358

[22] Filed: Oct. 29, 1993

[51] Int. Cl.⁶ ........................................... A61B 3/02
[52] U.S. Cl. ............................................ 351/242; 351/224
[58] Field of Search ............................ 351/242, 243, 351/246, 224, 225, 223

[56] References Cited

U.S. PATENT DOCUMENTS

| | | |
|---|---|---|
| 3,269,792 | 8/1966 | Mirsky . |
| 5,094,524 | 3/1992 | Fuhr . |
| 5,220,361 | 6/1993 | Lehmer et al. ................. 351/226 |
| 5,293,532 | 3/1994 | Marshall ........................ 351/246 |

FOREIGN PATENT DOCUMENTS 0361766  4/1990  European Pat. Off. .

Primary Examiner—William L. Sikes
Assistant Examiner—Hung Xuan Dang
Attorney, Agent, or Firm—Townsend and Townsend and Crew

[57] ABSTRACT

In a color field test where the field background is of a first color—preferably yellow—and the illuminating spot is of a second and different color—preferably blue, a translucent occluder is utilized for the eye. The translucent occluder is chosen to permit entry of light having the color of the background—here yellow—while filtering out substantially all light of the spot color—here blue. There results the ability to conduct a field test in color where retinal rivalry interference with the test is held to a minimum.

4 Claims, 2 Drawing Sheets

COLOR FIELD TEST WITH OCCLUSION OF NON-TESTED EYE

This invention relates to field tests for testing the peripheral vision of the human eye. More specifically, a method and apparatus is disclosed for conducting a field test on one eye utilizing a first color background with a superimposed and different second color stimulus testing the eye's peripheral vision. The improvement relates to the non-tested eye, this eye being occluded in the first color background to avoid the effects of retinal rivalry.

BACKGROUND OF THE INVENTION

This invention relates to the survey of the peripheral field of vision of the human eye utilizing an instrument known as a visual field tester.

A visual field tester surveys the sensitivity of a patient's retina. In what is called a static threshold test, a spot of light, termed the stimulus, is projected to a hemispherical projection screen for a short period of time. A patient viewing the hemispherical projection screen from the center of the sphere fixates along a line of sight to a fixation light source mounted on the surface of the bowl. The point of projection on the hemispherical projection screen is changed in a controlled fashion from one point to another in a predetermined pattern of points spaced apart from the fixation point. The intensity of light at a point varies from presentation to presentation in a controlled fashion. Preferably, the point is varied in intensity as the point moves from position to position on the hemispherical projection screen. A subjective determination is made by the patient in depressing a response button, if the stimulus is seen. By positioning the point to known locations on the hemispherical projection screen and changing the brightness (in a total amount of about four decades), the sensitivity of the patient's retina is measured and mapped.

It is known to provide occlusion of the non-tested eye in "white light" field testing of the human eye. This is necessary to ensure that the patient is only responding to light entering the tested eye. Specifically, and from about 1984, it has been known to conduct field tests by occluding the non-tested eye with a white light translucent patch. This white light translucent patch furnishes the non-tested eye with a background illumination similar to that background illumination seen by the tested eye but destroys contrast to the extent that the stimulus cannot be detected. This technique has been used with the reasoning that the provision of a white light background to the untested eye prevents retinal rivalry from obscuring the results of the test.

Retinal rivalry is a phenomenon in some patients where one eye, which is not the subject of test, interferes with the vision of the eye being tested. Retinal rivalry most frequently occurs when the eye not being tested is completely obscured so that the patient sees nothing—and the eye transmits a "black field" to the brain. Specifically, and while the patient being tested is trying to see and participate in a vision test of one eye, this eye is perceived by the patient to become either periodically dark or completely dark. The patient sees nothing. This phenomenon is particularly pronounced where a patient has a so-called "dominant eye" where one eye undertakes the transmission of most of the patient's visual information to the brain.

In attempts to avoid this phenomenon in white light tests, so-called translucent occluders have been utilized. Unfortunately, such translucent occluders utilized in white light field tests have not been completely satisfactory, since the white light field test includes presenting a relatively brilliant stimulus to the patient. Taking the case where the field of vision of the tested eye is either at or below threshold at a tested point, it is possible for the patient being tested to respond using the untested eye to the relatively bright light source passing through the diffuse eye occluder. The person conducting the examination does not know whether the response is due to light being seen by the tested eye or to a "flash" being seen at the non-tested eye through the translucent white light occluder.

Recently, field tests have been expanded to include non white light field testing. An example of this is field tests conducted with a yellow background light with a relative bright point being presented in blue. Such tests are believed more effective in locating early symptoms of eye disease, such as glaucoma.

DISCOVERY

I have discovered that field tests conducted with spots of blue color on backgrounds of yellow are particularly susceptible to retinal rivalry.

SUMMARY OF THE INVENTION

In a color field test where the field background is of a first color—preferably yellow—and the illuminating spot is of a second and different color—preferably blue— translucent occluder is utilized for the eye. The translucent occluder is chosen to permit entry of light having the color of the background—here yellow—while filtering out substantially all light of the spot color—here blue. There results the ability to conduct a field test in color where retinal rivalry interference with the test is held to a minimum.

DESCRIPTION OF THE PREFERRED EMBODIMENT

Figure 1A:
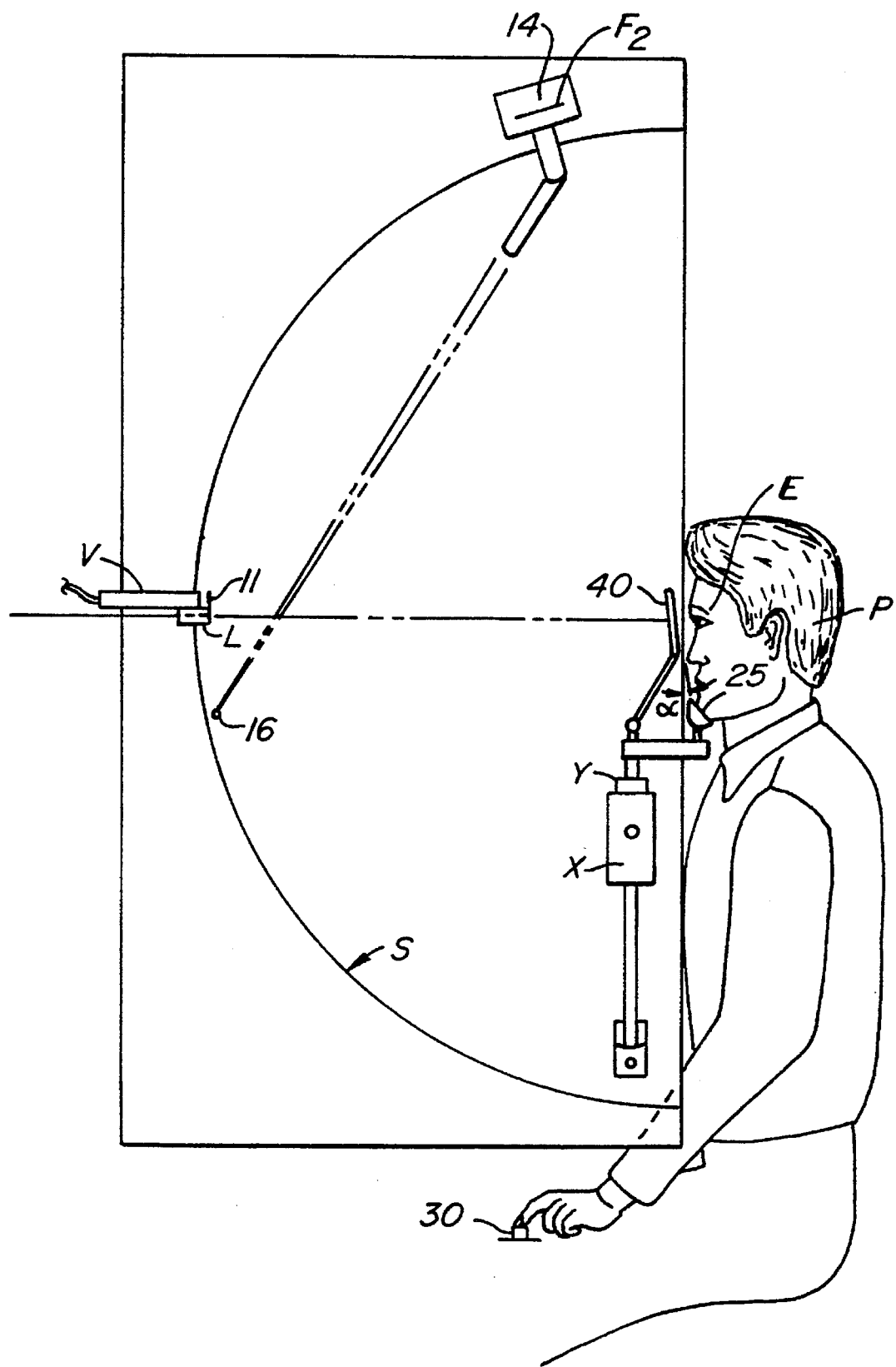
FIG. 1A is a side elevation section of a field test unit illustrating a patient undergoing a field test.
Figure 1B:
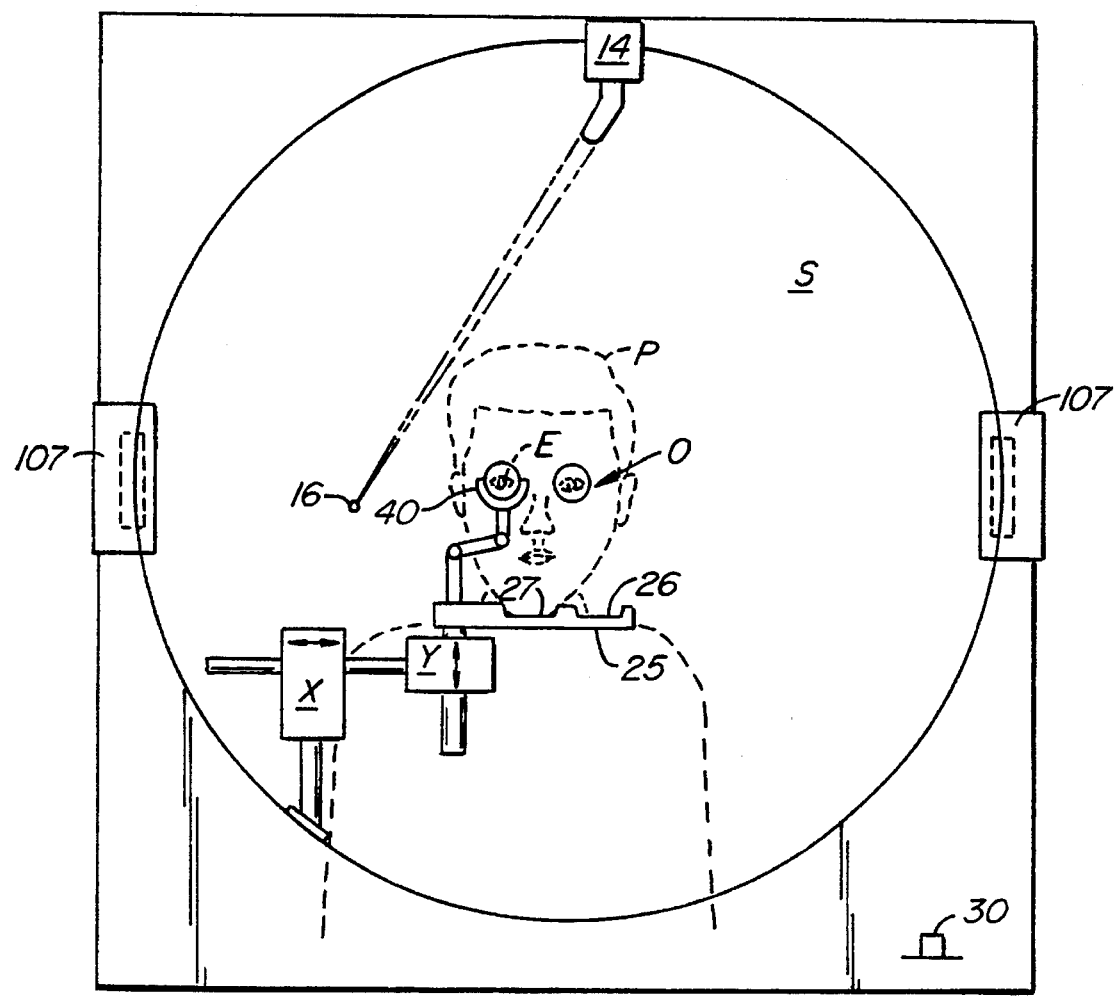
FIG. 1B is a rear elevation of the patient and field test apparatus of FIG. 1A; and, FIG. 2 is a perspective view of a colored translucent field test occluder utilized with this invention.

Referring to FIGS. 1A and 1B, a schematic of trial lens holder 40 of this invention is illustrated. A patient P is illustrated observing a hemispherical projection screen S. Patient P is here illustrated having left eye E being tested. In this test the patient P has been directed to fixate on the fixation light L at the center of the hemispheric projection screen.

Referring to FIG. 1B, the chin rest 25 illustrated has two indentations, these indentations including indentation 26 for testing the patient's right eye and indentation 27 for testing the patient's left eye. Projector 14 under the control of a computer (not shown) well known and understood in the prior art, projects spot 16 of the light on the surface of the hemispherical projection screen. The patient indicates that the spot 16 of light was seen by depressing response button 30. The response of the patient in pressing the button is recorded and mapped by apparatus well known and understood in the prior art.

The field test apparatus illustrated is old. It may be purchased from Humphrey Instruments, Inc. of San Leandro, Calif., USA under the designation Field Analyzer Series 600.

Referring to FIG. 1B, background illumination is provided by light sources 107. The background illumination is quite bright, set at between 100 cd/m$^2$ and 200 cd/m$^2$ and has the blue end of the spectrum removed with a 50% transmission cut-off set at 530 nanometers. Filters are schematically shown at $F_1$.

This background light—herein called yellow light—strongly excites the middle and long wave length retinal cone receptors, but weakly if at all excites the short wave length cone receptors of the eye.

Stimulus from projector 14 at point 16 is a spot which subtends 104 minutes of arc (1° 44') on the retina. This spot is created in a bright blue light which in the normal eye is readily visible in normal fields of peripheral vision. This is done by placing a narrow band dichroic filter centered at 440 nanometers in the projection path, this filter being schematically shown at $F_2$.

This projected stimulus—herein called blue—strongly excites the short wave length retinal cone receptors, but weakly excites the middle and long wave length cone receptors.

Figure 2:
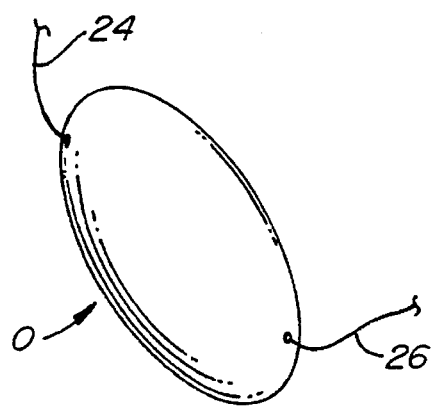

Referring to FIGS. 1B and 2, a translucent eye occluder O is utilized. In FIG. 2, such an occluder O is shown with bands 24, 26 for fastening to the head of the patient P. This occluder can be yellow or orange and has two characteristics of importance.

First, transmission is chosen so that light with a wavelength of less than 520 nm is excluded. It is preferred that the patch transmit with efficiency light with a wave length longer than 520 nm.

Secondly, the patch must fit closely over the eye so that no extraneous light enters the eye. Preferably, the patch will used a foam sealing strip on the edge which will directly and conformably abut the skin without appreciable light leakage.

Finally, the patch must be translucent to the background light but prevent the non-tested eye from seeing the fixation light.

It will be noted that this distinguishes from test in white light. Specifically, and with the light of the spot excluded, no extraneous flash of light can be seen by the patient which can be mistaken for peripheral illumination.

What is claimed is:

1. In a field test for the human eye of a patient wherein:

a background field is illuminated;

means for having said patient fixate the human eye being tested in a first direction;

means for providing a light stimulus presented to a patient at a known location which non co-axial to said fixation of said human eye;

means for recording signals from said patient of recognition of said light stimulus;

means for providing said light stimulus in a first color; and means for providing said background illumination in a second color exclusive of said first color;

the improvements comprising:

means for occluding, excluding the non-tested eye of said patient in said first color, said means for transmitting all light of said second color.

2. In a field test for the human eye of a patient according to claim 1 and wherein:

said first color, called blue, strongly excites the short wavelength retinal cone receptors, but weakly excites the middle and long wavelength cone receptors;

said second color, called yellow, strongly excites the middle and long wavelength retinal cone receptors, but weakly if at all excites the short wavelength cone receptors.

3. A method of field testing one eye of a human patient utilizing a light stimulus on background illumination within a field of view of said eye comprising the steps of:

providing said light stimulus in a first color;

providing said background illumination in a second color exclusive of said first color; and, occluding the non-tested eye of said patient in said first color, and transmitting all light of said second color.

4. The method of field testing one eye of a human patient utilizing a light stimulus on background illumination within a field of view of said eye comprising the steps of:

providing said light stimulus in blue;

providing said background illumination in yellow;

providing an occluder for the non-tested eye; and, selecting the material of said occluder to occlude the non-tested eye of said patient in blue and transmit said yellow light to the non-tested eye of said patient.

* * * * *